(12) United States Patent
Touchi et al.

(10) Patent No.: US 9,378,924 B2
(45) Date of Patent: Jun. 28, 2016

(54) CHARGED PARTICLE BEAM TREATMENT APPARATUS

(71) Applicant: SUMITOMO HEAVY INDUSTRIES, LTD., Tokyo (JP)

(72) Inventors: Yutaka Touchi, Niihama (JP); Junichi Inoue, Niihama (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 0 days.

(21) Appl. No.: 14/658,301

(22) Filed: Mar. 16, 2015

(65) Prior Publication Data

US 2015/0270097 A1 Sep. 24, 2015

(30) Foreign Application Priority Data

Mar. 19, 2014 (JP) ................. 2014-055977

(51) Int. Cl.
*G21K 5/04* (2006.01)
*H01J 37/304* (2006.01)
*H01J 37/147* (2006.01)
*A61N 5/10* (2006.01)

(52) U.S. Cl.
CPC .............. *H01J 37/304* (2013.01); *A61N 5/1067* (2013.01); *A61N 5/1043* (2013.01); *A61N 5/1081* (2013.01); *A61N 2005/1087* (2013.01); *H01J 37/1474* (2013.01); *H01J 2237/15* (2013.01); *H01J 2237/30483* (2013.01)

(58) Field of Classification Search
USPC ........ 250/396 R, 397, 396 ML, 492.1, 492.2, 250/492.3; 315/500, 501, 502, 503, 504, 315/505; 600/1
See application file for complete search history.

(56) References Cited

U.S. PATENT DOCUMENTS

2006/0226372 A1* 10/2006 Yanagisawa ............. A61N 5/10
250/396 R

FOREIGN PATENT DOCUMENTS

JP 2011-191184 A 9/2011

* cited by examiner

*Primary Examiner* — Nicole Ippolito
(74) *Attorney, Agent, or Firm* — Squire Patton Boggs (US) LLP

(57) ABSTRACT

A charged particle beam treatment apparatus includes: a cyclotron configured to accelerate charged particles while turning the charged particles along a predetermined orbital plane; an irradiation portion configured to irradiate an irradiation object with a charged particle beam while scanning the charged particle beam emitted from the cyclotron; a measurement portion configured to measure a dose of the charged particle beam emitted from the cyclotron; and a control portion. The cyclotron has a pair of chopper electrodes which can switch ON/OFF of the charged particle beam from the cyclotron by changing an orbit of the charged particles that pass through the orbit, and a power source configured to apply a voltage to the pair of chopper electrodes. The control portion controls a size of a voltage in at least any one of the pair of chopper electrodes based on the dose measured by the measurement portion.

5 Claims, 6 Drawing Sheets

CHARGED PARTICLE BEAM TREATMENT APPARATUS

RELATED APPLICATIONS

Priority is claimed to Japanese Patent Application No. 2014-055977, filed Mar. 19, 2014, the entire content of which is incorporated herein by reference.

BACKGROUND

1. Technical Field

A certain embodiment of the present invention relates to a charged particle beam treatment apparatus.

2. Description of Related Art

In the related art, a charged particle beam treatment apparatus including an irradiation portion emitting a charged particle beam (line scanning beam), a scanning electromagnet which scans the charged particle beam, and a control portion which controls an operation of the scanning electromagnet are disclosed.

SUMMARY

According to an embodiment of the present invention, there is provided a charged particle beam treatment apparatus including: a cyclotron configured to accelerate charged particles while turning the charged particles along a predetermined orbital plane; an irradiation portion configured to irradiate an irradiation object with a charged particle beam while scanning the charged particle beam emitted from the cyclotron; a measurement portion configured to measure a dose of the charged particle beam emitted from the cyclotron; and a control portion configured to control an operation of the cyclotron. The cyclotron has a pair of chopper electrodes which can switch ON/OFF of the charged particle beam from the cyclotron by changing an orbit of the charged particles that pass through the orbit, and a power source configured to apply a voltage to the pair of chopper electrodes. The control portion controls a size of a voltage in at least any one of the pair of chopper electrodes based on the dose measured by the measurement portion.

DETAILED DESCRIPTION

Figure 1:
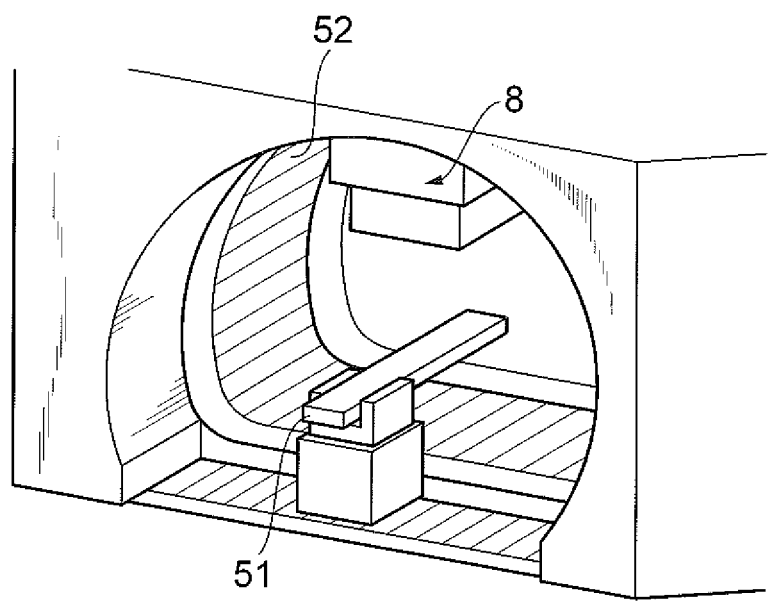
FIG. 1 is a perspective view showing a charged particle beam treatment apparatus.

The above-described charged particle beam treatment apparatus irradiates an irradiation object with a charged particle beam while scanning along a predetermined line. A dose of the charged particle beam emitted to the irradiation object can be uniform as a whole. When the irradiation dose of the charged particle beam changes when scanning the charged particle beam, unevenness in the dose of the charged particle beam emitted to the irradiation object occurs.

It can also be considered that the amount of ions (charged particles) emitted from an ion source is adjusted by controlling the generation quantity of arcs generated in the ion source in accordance with the change in the irradiation dose of the charged particle beam. However, it is difficult to control the concentration of plasma in the ion source with high accuracy and good responsiveness.

Therefore, the embodiment of the present invention describes the charged particle beam treatment apparatus capable of suppressing the change in the irradiation dose of the charged particle beam during scanning.

In the charged particle beam treatment apparatus according to the embodiment of the present invention, the control portion controls a size of a voltage in at least any one of a pair of chopper electrodes based on a dose measured by a measurement portion. For this reason, when a change in the dose measured by the measurement portion is caused, the size of the voltage in at least any one of the pair of chopper electrodes is changed with high accuracy and good responsiveness. Accordingly, an electric field between the pair of chopper electrodes is changed, and therefore, the orbit of the charged particles passing through the pair of chopper electrodes is changed. Accordingly, the dose of the charged particle beam emitted from the cyclotron is also changed as the orbit of the charged particles in the cyclotron is changed. Therefore, it is possible to suppress the change in the irradiation dose of the charged particle beam during scanning.

The pair of chopper electrodes may be disposed in the cyclotron such that the orbital plane is positioned therebetween. In this case, the chopper electrodes do not intersect the orbital plane, and therefore, it is possible to prevent the movement of the charged particles in the cyclotron from being interfered with the chopper electrodes.

The control portion may control a difference in a voltage between the pair of chopper electrodes based on the dose measured by the measurement portion. In this case, it is possible to suppress the change in the irradiation dose of the charged particle beam with higher accuracy and better responsiveness.

The charged particle beam treatment apparatus according to the embodiment of the present invention may further include a switch disposed between a power source and the chopper electrodes. The control portion may control ON/OFF of the switch. In this case, it is possible to further suppress the change in the irradiation dose of the charged particle beam with higher accuracy and better responsiveness.

The control portion may control an ON/OFF duty ratio of the switch.

An embodiment of the present invention will be described with reference to the accompanying drawings. However, the following embodiment is an example for describing the embodiment of the present invention, and is not intended to be limited to the following content. In the description, identical elements or elements having the same functions are given the same reference numerals, and the repeated description will be omitted.

Figure 2:
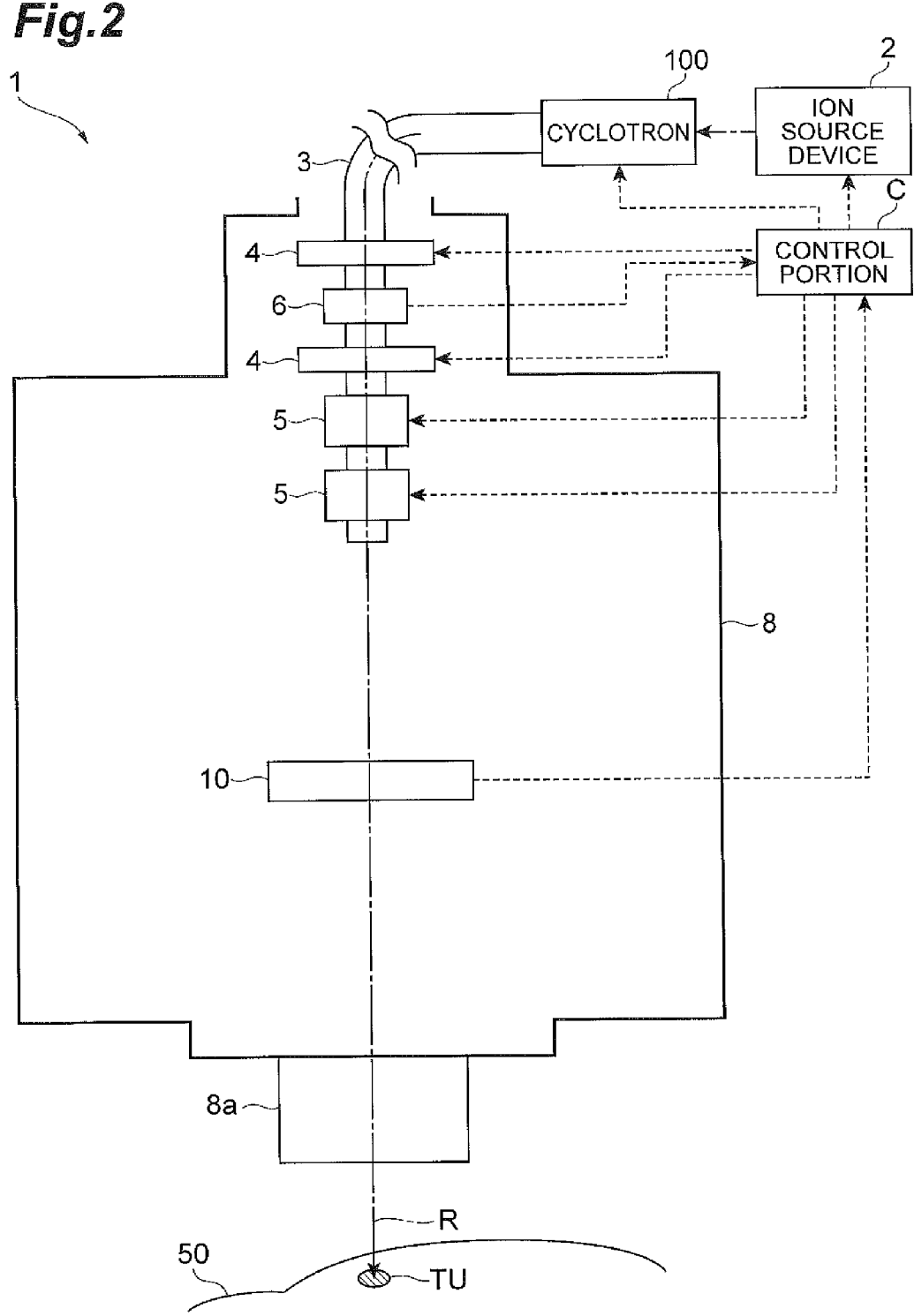
FIG. 2 is a view schematically showing a configuration of the charged particle beam treatment apparatus.

As shown in FIGS. 1 and 2, a charged particle beam treatment apparatus 1 includes an ion source device 2, a cyclotron 100, a beam transport portion 3, a rotary gantry 52, and an irradiation nozzle 8 (irradiation portion). The cyclotron 100 is an accelerator which generates a charged particle beam R by accelerating charged particles generated in the ion source device 2. The charged particle beam R is a beam which is obtained by accelerating particles having electrical charges at a high speed. Examples of the charged particle beam R include a proton beam, a heavy particle (heavy ion) beam, and an electron beam.

A patient 50 on a treatment table 51 is irradiated with a charged particle beam R emitted from the cyclotron 100 through the beam transport portion 3. A quadrupole electromagnet 4, a beam position monitor 6, a quadrupole electromagnet 4, scanning electromagnets 5 and 5, and a dose measurement device 10 are provided around the beam transport portion 3 from an upstream side (cyclotron 100 side) to an downstream side (treatment table 51 side). The quadrupole electromagnet 4, the beam position monitor 6, the quadrupole electromagnet 4, the scanning electromagnets 5 and 5, and the dose measurement device 10 are accommodated in the irradiation nozzle 8 (irradiation portion) together with the beam transport portion 3.

As shown in FIG. 1, the irradiation nozzle 8 is attached to the rotary gantry 52 which is provided so as to surround the treatment table 51. The irradiation nozzle 8 is rotatable around the treatment table 51 using the rotary gantry 52. The irradiation nozzle 8 irradiates an irradiation object such as a tumor TU (refer to FIG. 2) existing in the body of the patient 50 (refer to FIG. 2) laid on the treatment table 51 with a charged particle beam R.

The quadrupole electromagnet 4 suppresses scattering of the charged particle beam R emitted from the cyclotron 100 to the beam transport portion 3 and converges the charged particle beam R.

The scanning electromagnet 5 scans the charged particle beam R in an X-direction and a Y-direction. For this reason, the tumor TU existing in the body of the patient 50 is continuously irradiated with the charged particle beam R, which is emitted from a tip end 8a of the irradiation nozzle 8, along a predetermined irradiation line using a scanning system. More specifically, the inside of an irradiation field which is set in each layer of the tumor TU is continuously irradiated with the charged particle beam R while the charged particle beam R is scanned by the scanning electromagnet 5 (that is, raster-scanned or line-scanned) when the tumor TU is divided into a plurality of layers in a depth direction (irradiation direction). The charged particle beam R is a pencil beam used in the scanning system.

The beam position monitor 6 detects an irradiation position of the charged particle beam R in the X-direction and the Y-direction. The dose measurement device 10 measures the dose and a dose distribution of the charged particle beam R emitted to the patient 50 on the treatment table 51.

The charged particle beam treatment apparatus 1 includes a control portion C. The control portion C is an electronic control unit having a CPU, a ROM, a RAM, and the like, and comprehensively controls the charged particle beam treatment apparatus 1.

Figure 3:
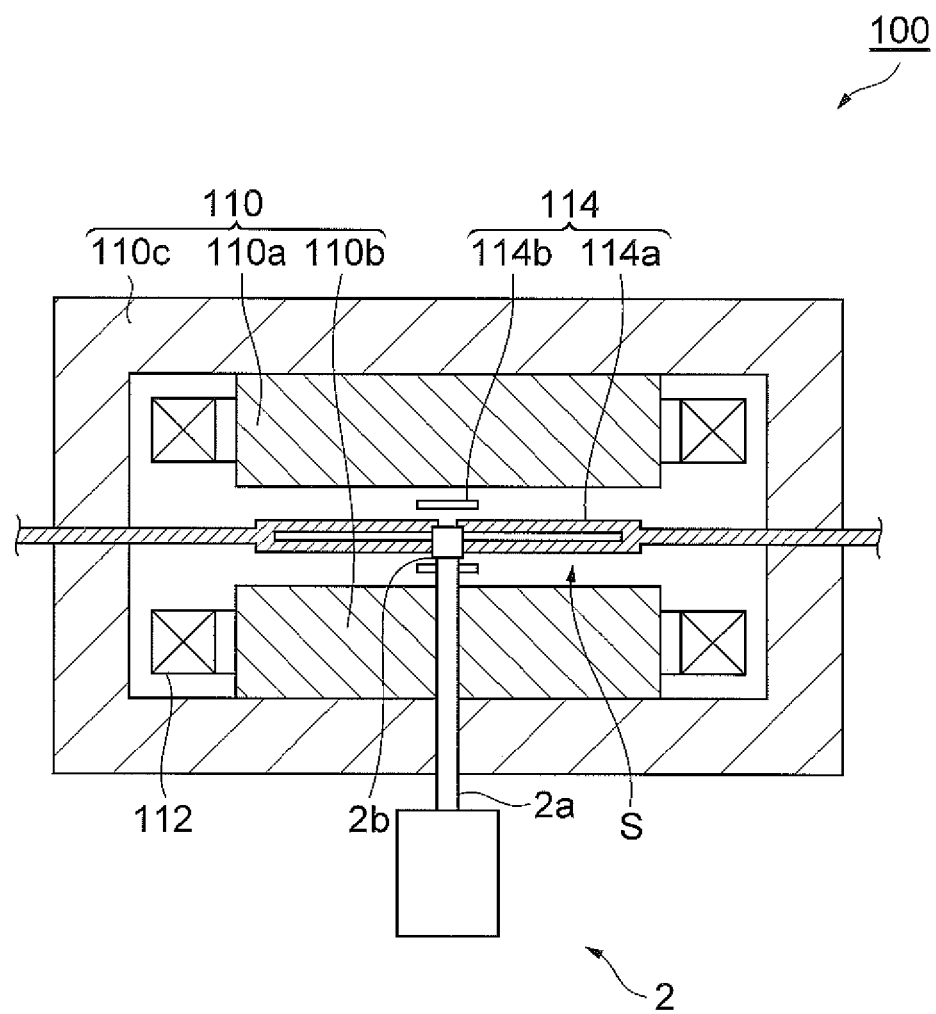
FIG. 3 is a view schematically showing a cross section of a cyclotron.
Figure 4:
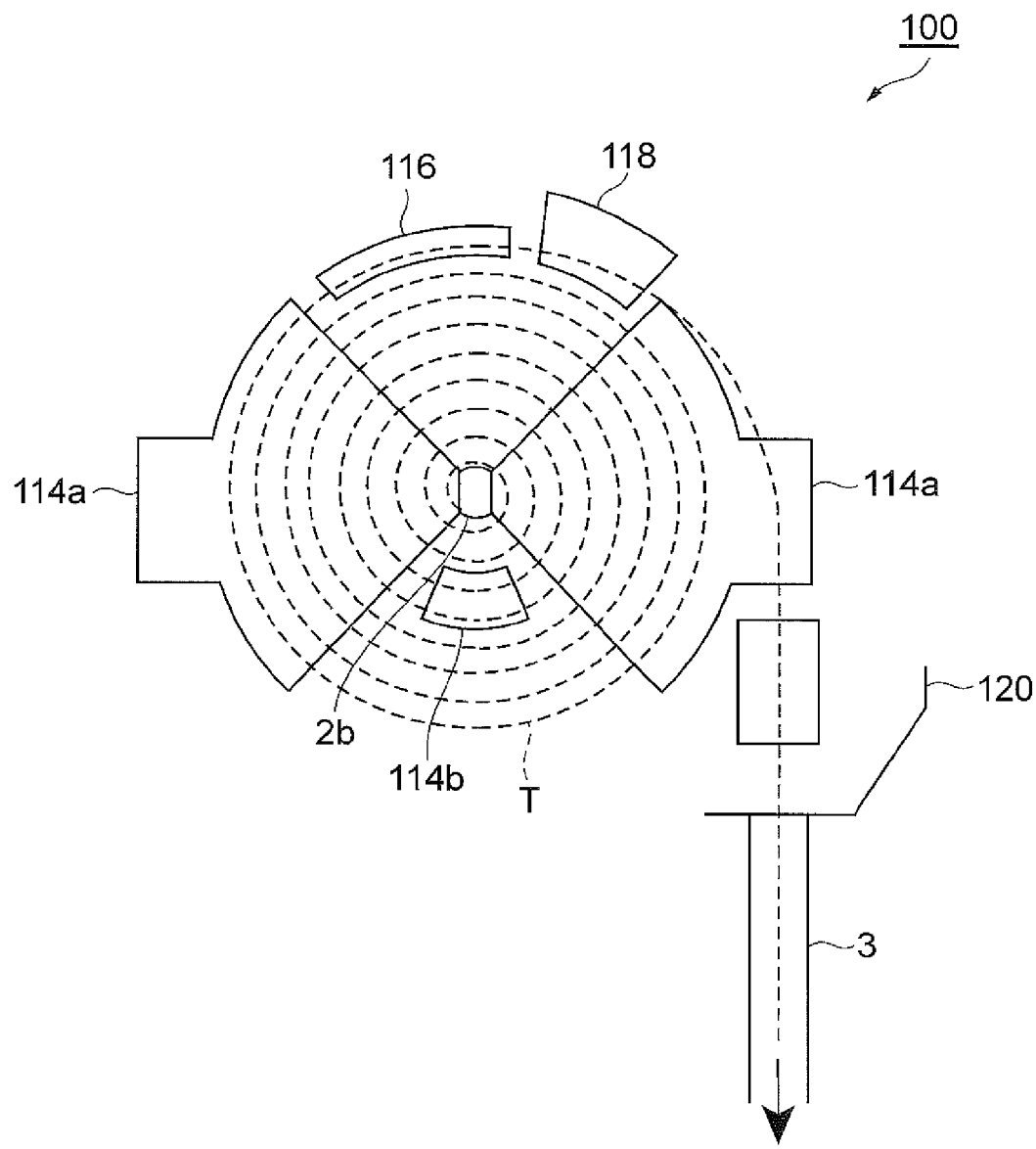
FIG. 4 is a view schematically showing the inside of the cyclotron seen from above.

Next, a configuration of the cyclotron 100 will be described with reference to FIGS. 3 to 5. As shown in FIG. 3, the cyclotron 100 includes a core 110, a coil 112, and a high frequency generator 114. The core 110 has a pair of an upper pole portion 110a and a lower pole portion 110b which face each other and form a main magnetic field; and a yoke portion 110c which magnetically connect the upper pole portion 110a and the lower pole portion 110b The upper pole portion 110a and the lower pole portion 110b are positioned in a vacuum chamber (not shown), the inside of which is made vacuous.

When charged particles generated in the ion source device 2 reach a central portion of the cyclotron 100 through a conduit 2a, the direction of the charged particles is bent from a vertical direction to a horizontal direction by an inflector 2b positioned at a tip end portion of the conduit 2a. Next, the charged particles are turned and accelerated while drawing a circular orbit (spiral orbit from the central portion of the cyclotron 100 to the outside) T along a predetermined orbital plane (median plane) due to a magnetic field formed by the core 110 and the coil 112 (refer to FIG. 4). That is, the area between the upper pole portion 110a and the lower pole portion 110b functions as an acceleration space S (refer to FIG. 3) of the charged particles. Then, the orbit T of the charged particles is finely adjusted by a deflector 116 or a magnetic channel 118, and the charged particle beam R emitted through a beam outlet 120 is introduced to the beam transport portion 3 (refer to FIG. 4). The ion source device 2 may be disposed inside the cyclotron 100. In this case, the inflector 2b or the like is unnecessary.

Returning to FIG. 3, the coil 112 is used for forming the main magnetic field. The coil 112 includes a first portion which is disposed so as to surround the periphery of the upper pole portion 110a; and a second portion which is disposed so as to surround the periphery of the lower pole portion 110b. The first and second portions are electrically connected to each other in series.

The high frequency generator 114 has, for example, a pair of dee electrodes 114a having a fan shape, and a pair of chopper electrodes 114b. All of the pair of dee electrodes 114a and the pair of chopper electrodes 114b are disposed between the upper pole portion 110a and the lower pole portion 110b, that is, in the acceleration space S. The pair of dee electrodes 114a faces each other such that the orbital plane is positioned therebetween. The pair of chopper electrodes 114b faces each other such that the orbital plane is positioned therebetween and is positioned between the pair of dee electrodes 114a when seen from a direction perpendicular to the orbital plane (refer to FIGS. 3 and 4).

The dee electrodes 114a are connected to a high frequency power source (not shown). The high frequency power source supplies high frequency electric power to the dee electrodes 114a to generate an AC electric field (high frequency electric field), in which the cycle of the electric field is exchanged at a constant cycle, between the dee electrodes 114a. The charged particles are accelerated every time the charged particles pass the dee electrodes 114a by synchronizing the timing at which the charged particles pass through the dee electrodes 114a and the cycle of the high frequency electric field.

Figure 5:
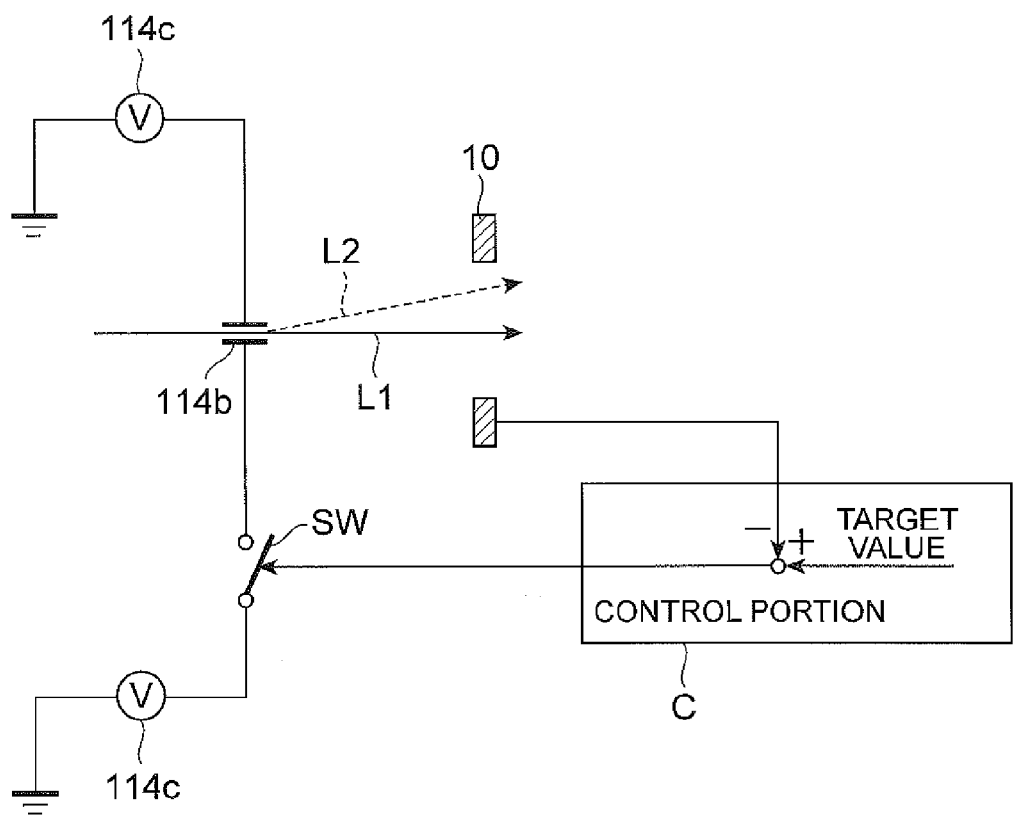
FIG. 5 is a functional block view for illustrating ON/OFF control of a switch.

As shown in FIG. 5, power sources 114c are connected to respective chopper electrodes 114b. One power source 114c may be connected to the chopper electrodes 114b. The power source 114c applies, for example, a voltage of 5 kV to each of the chopper electrodes 114b. A power source capable of carrying out high-speed response may be used as the power source 114c. A switch SW is disposed between a chopper electrode 114b and a power source 114c. The switch SW switches ON/OFF based on a control signal from the control portion C. When the switch SW is completely turned off, the difference in a voltage between the pair of chopper electrodes 114b becomes large. Therefore, charged particles passing through the pair of chopper electrodes 114b are largely bent. For this reason, the charged particle beam R is not emitted from an accelerator 100. Accordingly, the control portion C controls an emission state of the charged particle beam R from the cyclotron 100, that is, ON/OFF of the charged particle beam R by switching ON/OFF of the switch SW.

Meanwhile, when so-called chopper control is performed by the control portion C and ON/OFF of the switch SW is switched at a high speed, the effective value of the voltage generated in the chopper electrode 114b to which the switch SW is connected becomes a value which is different from the voltage (5 kV) of the power source 114c. Specifically, when a step-down chopper circuit is configured around the switch SW, the effective value of the voltage generated in the chopper electrode 114b becomes smaller than the voltage (5 kV) of the power source 114c. On the other hand, when a step-up chopper circuit is configured around the switch SW, the effective value of the voltage generated in the chopper electrode 114b becomes greater than the voltage (5 kV) of the power source 114c. The control portion C may also perform PWM control in which the pulse width is arbitrarily changed by adjusting the ON/OFF duty ratio of the switch, in addition to the chopper control. When the PWM control is performed together, a transient response is suppressed, and therefore, it is possible to improve stability of the control system.

When the chopper control is performed by the control portion C as described above, the charged particles passing through the pair of chopper electrodes 114b linearly advance (refer to a solid line L1 in FIG. 5) or are deflected (refer to a dashed line L2 in FIG. 5) in accordance with the difference in the voltage between the pair of chopper electrodes 114b. When the orbit of the charged particles is changed by the pair of chopper electrodes 114b, the acceleration efficiency of the charged particles in the cyclotron 100 is also changed in accordance with the degree of the change. As a result, the dose of the charged particle beam R measured by the dose measurement device 10 is also changed.

When the control portion C receives data relating to the dose of the charged particle beam R measured by the dose measurement device 10, the control portion C compares the received dose with a target value. As a result of the comparison, when the received dose exceeds the target value, the control portion C switches ON/OFF of the switch SW such that the dose of the charged particle beam R measured by the dose measurement device 10 becomes small. In this manner, the control portion C performs feedback control on the switch SW such that the charged particle beam R measured by the dose measurement device 10 approaches the target value.

Figure 6:
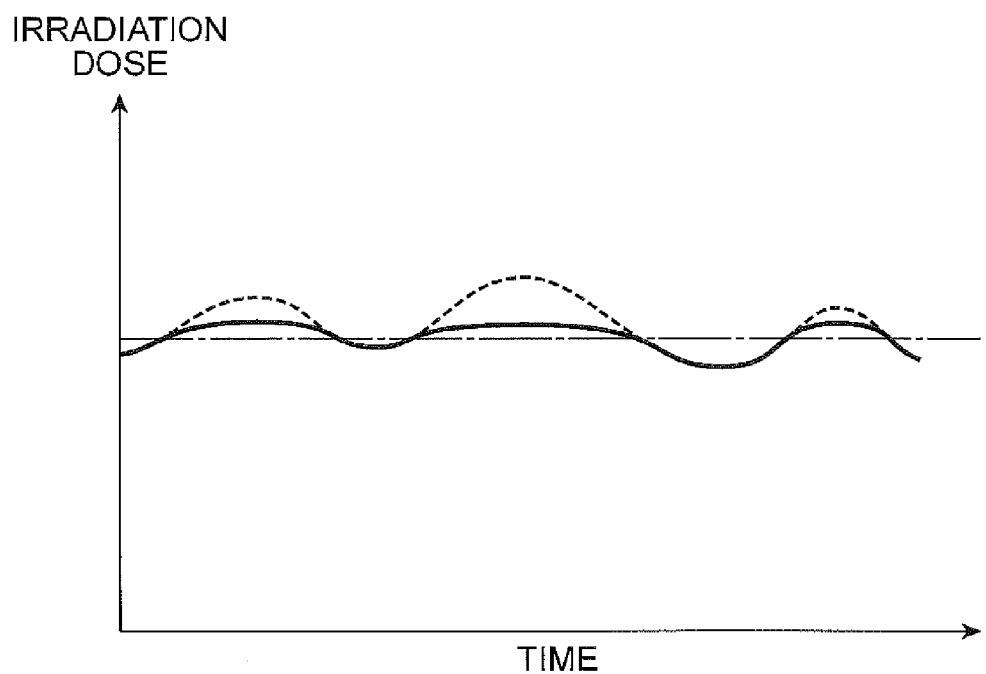
FIG. 6 is a view showing a change in an irradiation dose with respect to time as an example.

The difference in a change in the irradiation dose depending on whether or not the above-described feedback control is performed is shown in FIG. 6 as an example. In FIG. 6, the alternating long and short dashed line represents the target value, the dashed line represents a change in irradiation dose when the feedback control is not performed, and the solid line represents a change in irradiation dose when the feedback control is performed. As shown in FIG. 6, the change in the irradiation dose is controlled such that the irradiation dose approaches the target value by the above-described feedback control performed by the control portion C.

In the embodiment as described above, the control portion C controls the size of the voltage in at least any one of the pair of chopper electrodes 114b based on the dose measured by the dose measurement device 10. For this reason, when a change in the dose measured by the dose measurement device 10 is caused, the size of the voltage in at least any one of the pair of chopper electrodes 114b is changed with high accuracy and good responsiveness. Accordingly, the electric field between the pair of chopper electrodes 114b is changed, and therefore, the orbit of the charged particles passing through the pair of chopper electrodes 114b is changed. Accordingly, the dose of the charged particle beam R emitted from the cyclotron 100 is also changed as the orbit of the charged particles in the cyclotron 100 is changed. Therefore, it is possible to suppress the change in the irradiation dose of the charged particle beam R during scanning.

In the embodiment, the pair of chopper electrodes 114b is disposed in the cyclotron 100 such that the orbital plane (median plane) is positioned therebetween. For this reason, the chopper electrodes 114b do not intersect the orbital plane, and therefore, it is possible to prevent the movement of the charged particles in the cyclotron 100 from being interfered with the chopper electrodes 114b.

In the embodiment, the control portion C chopper-controls the difference in the voltage between the pair of chopper electrodes 114b based on the dose measured by the dose measurement device 10. For this reason, it is possible to suppress the change in the irradiation dose of the charged particle beam R with higher accuracy and better responsiveness.

Hereinbefore, the embodiment is described in detail, but the embodiment of the present invention is not limited to the above-described embodiment. For example, the pair of chopper electrodes 114b may face each other in the cyclotron 100 so as to intersect the orbital plane (median plane).

In the above-described embodiment, the control portion C changes the effective value of the voltage generated in the chopper electrodes 114b connected to the switch SW by switching ON/OFF of the switch SW. However, a power source (for example, a dropper power source) capable of changing an output voltage may be connected to the chopper electrodes 114b and the control portion C may cause to change the output voltage by controlling the power source.

It should be understood that the invention is not limited to the above-described embodiment, but may be modified into various forms on the basis of the spirit of the invention. Additionally, the modifications are included in the scope of the invention.

What is claimed is:

1. A charged particle beam treatment apparatus comprising:
   a cyclotron configured to accelerate charged particles while turning the charged particles along a predetermined orbital plane;
   an irradiation portion configured to irradiate an irradiation object with a charged particle beam while scanning the charged particle beam emitted from the cyclotron;
   a measurement portion configured to measure a dose of the charged particle beam emitted from the cyclotron; and
   a control portion configured to control an operation of the cyclotron,
   wherein the cyclotron has a pair of chopper electrodes which can switch ON/OFF of the charged particle beam from the cyclotron by changing an orbit of the charged particles that pass through the orbit, and a power source configured to apply a voltage to the pair of chopper electrodes, and
   wherein the control portion controls a size of a voltage in at least any one of the pair of chopper electrodes, such that the dose of the charged particle beam measured by the measurement portion is reduced when the dose measured by the measurement portion surpasses a target value.

2. The charged particle beam treatment apparatus according to claim 1,
   wherein the pair of chopper electrodes are arranged in the cyclotron such that the orbital plane is positioned therebetween.

3. The charged particle beam treatment apparatus according to claim 1,
   wherein the control portion controls a difference in a voltage between the pair of chopper electrodes based on the dose measured by the measurement portion.

4. The charged particle beam treatment apparatus according to claim 3, further comprising:
   a switch disposed between the power source and the chopper electrodes, wherein the control portion controls ON/OFF of the switch.

5. The charged particle beam treatment apparatus according to claim 4,
wherein the control portion controls an ON/OFF duty ratio of the switch.

\* \* \* \* \*